United States Patent [19]

Urban

[11] Patent Number: 5,359,068

[45] Date of Patent: Oct. 25, 1994

[54] PROCESSES AND INTERMEDIATES FOR THE PREPARATION OF 5-[2-(4-(BENZOISOTHIAZOL-3-YL)-PIPERAZIN-1-YL)ETHYL]-6-CHLORO-1,3-DIHYDRO-INDOL-2-ONE

[75] Inventor: Frank J. Urban, Waterford, Conn.

[73] Assignee: Pfizer Inc., New York, N.Y.

[21] Appl. No.: 83,429

[22] Filed: Jun. 28, 1993

[51] Int. Cl.$^5$ .......................................... C07D 417/00
[52] U.S. Cl. .................... 544/368; 544/358; 544/399; 548/486
[58] Field of Search ................ 548/486; 544/368, 358, 544/399

[56] References Cited

U.S. PATENT DOCUMENTS

| | | | |
|---|---|---|---|
| 4,569,942 | 2/1986 | Kadin | 514/414 |
| 4,690,943 | 9/1987 | Kadin | 514/418 |
| 4,721,712 | 1/1988 | Kadin | 514/253 |
| 4,831,031 | 5/1989 | Lowe, III et al. | 544/368 |
| 4,952,584 | 8/1990 | Thompson et al. | 514/292 |

OTHER PUBLICATIONS

Wang et al, Chem Abst. 119:138892z (1993).
RajanBabu et al, CA 104(23):207092t (1986).
Flitsch et al, CA 104(5):33928c (1985).
Kosuge et al. CA 104(1):5731q (1985).
March, Advanced Org. Chem. 3rd Edition, 1985 pp. 312, 313, 334, 335, 348, 413, 491, 788.
Sundberg, The Chemistry of Indoles, 1970, pp. 180, 181.

Primary Examiner—Cecilia Tsang
Attorney, Agent, or Firm—Peter C. Richardson; Paul H. Ginsburg; Seymour G. Bekelnitzky

[57] ABSTRACT

A process for preparing the compound of the formula

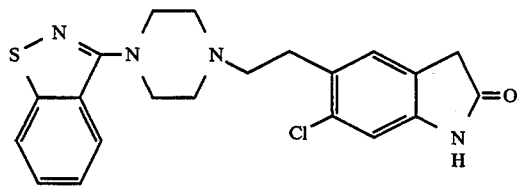

I which comprises treating a compound of the formula

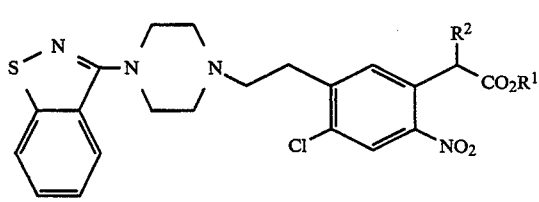

II wherein $R^2$ is hydrogen, CN or $CO_2R^1$ and $R^1$ is hydrogen or ($C_1$-$C_6$)alkyl with a reducing agent with the proviso that when $R^2$ is CN or $CO_2R^1$ and $R^1$ is ($C_1$-$C_6$)alkyl the product of the reduction is heated with an acid. Compounds of formula II wherein $R^2$ is CN or $CO_2R^1$ and $R^1$ is ($C_1$-$C_6$)alkyl or $R^2$ is hydrogen and $R^1$ is ($C_1$-$C_6$)alkyl or hydrogen. The compound of formula VII $R^1$ is ($C_1$-$C_6$)alkyl. The compound of formula III. The compound of formula I is useful in the treatment of psychotic disorders.

17 Claims, No Drawings

PROCESSES AND INTERMEDIATES FOR THE PREPARATION OF 5-[2-(4-(BENZOISOTHIAZOL-3-YL)-PIPERAZIN-1-YL)ETHYL]-6-CHLORO-1,3-DIHYDRO-INDOL-2-ONE

BACKGROUND OF THE INVENTION

This invention relates to processes and intermediates for the its preparation of 5-[2-(4-(benzoisothiazol-3-yl)-piperazin-1-yl)ethyl]-6-chloro-1,3-dihydro-indol-2-one5-[2-(4-(benzoisothiazol-3-yl)-piperazin-1-yl)ethyl]-6-chloro-1,3-dihydro-indol-2-one is useful in the treatment of psychotic disorders.

5-[2-(4-(benzoisothiazol-3-yl)-piperazin-1-yl)ethyl]-6-chloro-1,3-dihydro-indol-2-one and a process for its preparation are disclosed in U.S. Pat. No. 4,831,031.

SUMMARY OF THE INVENTION

The present invention provides a process for preparing the compound of the formula

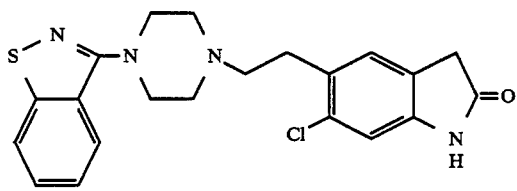

I which comprises treating a compound of the formula

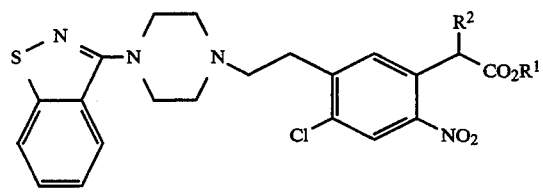

II wherein $R^2$ is hydrogen, CN or $CO_2R^1$ and $R^1$ is hydrogen or $(C_1-C_6)$alkyl with a reducing agent with the proviso that when $R^2$ is CN or $CO_2R^1$ and $R^1$ is $(C_1-C_6)$alkyl the product of the reduction is heated with an acid.

The invention also provides a process for preparing a compound of the formula II a) wherein $R^2$ and $R^1$ are both hydrogen by heating the compound of the formula II wherein $R^1$ is $(C_1-C_6)$alkyl and $R^2$ is CN or $CO_2R^1$ in the presence of an aqueous acid:

b) wherein $R^2$ is hydrogen and $R^1$ is $(C_1-C_6)$alkyl by
  i) treating a compound of the formula

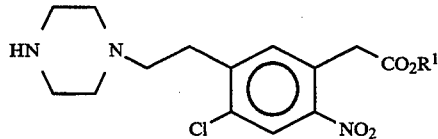

VII wherein $R^1$ is $(C_1-C_6)$alkyl with the compound of the formula

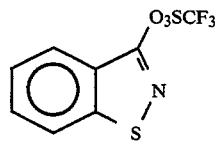

in the presence of a base; or
  ii) treating a compound of the formula II wherein $R^1$ and $R^2$ are both hydrogen with a $(C_1-C_6)$alkanol in the presence of an acidic esterification catalyst; or c) wherein $R^1$ is $(C_1-C_6)$alkyl and $R^2$ is CN or $CO_2R^1$ by treating the compound of the formula

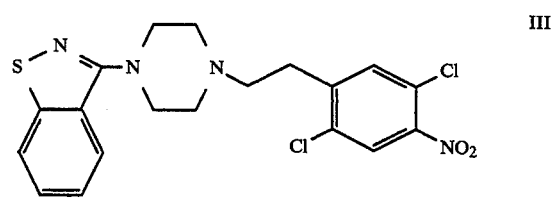

III with a compound of the formula $R^2-CH_2-CO_2R^1$, wherein $R^2$ is CN or $CO_2R^1$, respectively, and $R^1$ is $(C_1-C_6)$alkyl in the presence of a base.

In another aspect the invention provides a process for preparing the compound of the formula III by treating the compound of the formula

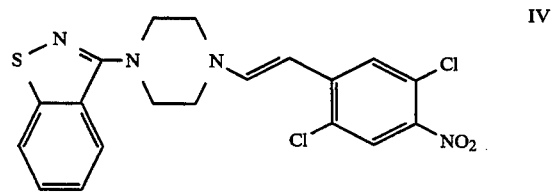

IV with a reducing agent.

According to another aspect of the invention there is provided a process for preparing the compound of formula IV which comprises treating the compound of the formula

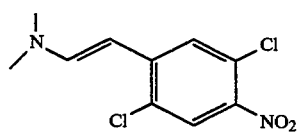

V with the compound of the formula

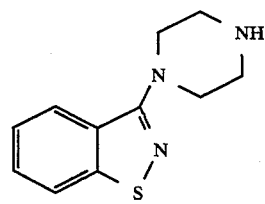

in the presence of a $(C_1-C_6)$ alkanoic acid.

Another aspect of the invention provides a process for preparing the compound of the formula V which comprises treating a compound of the formula

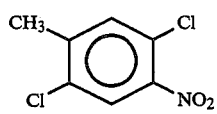

with an enamine forming compound selected from the group consisting of t-butoxybis(dimethylamino)methane and dimethylformamide dialkylacetals in an inert solvent.

Yet another aspect of the invention provides a process for preparing a compound of the formula VII by treating a compound of the formula

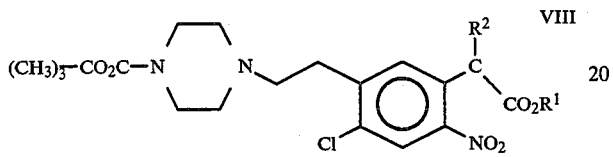

wherein $R^2$ is $CO_2R^1$ or CN and $R^1$ is $(C_1-C_6)$alkyl with an acid at an elevated temperature.

In accordance with another aspect of the invention there is provided a process for preparing a compound of the formula VIII which comprises treating the compound of the formula

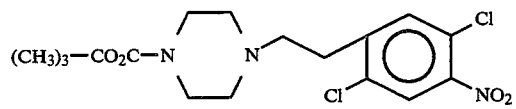

with a compound of the formula $R^2$—$CH_2$—$CO_2R^1$ wherein $R^2$ is $CO_2R^1$ or CN and $R^1$ is $(C_1-C_6)$alkyl in the presence of a base.

Another aspect of the invention provides a process for preparing the compound of the formula IX which comprises treating the compound of the formula

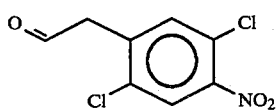

with the compound of the formula

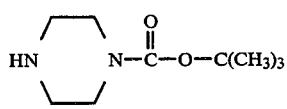

in the presence of $(CH_3CO_2)_3NaBH$ and acetic acid.

According to another aspect of the invention there is provided a process for preparing a compound of the formula X by treating the compound of formula V with oxalic acid.

Another aspect of the invention provides a process for preparing the compound of the formula

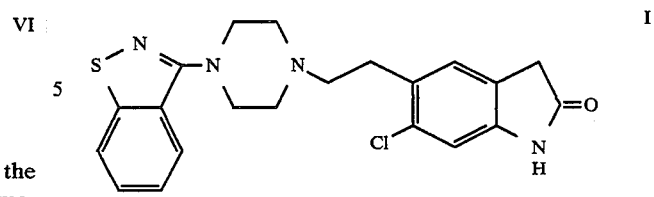

which comprises the steps of

I. treating a compound of the formula

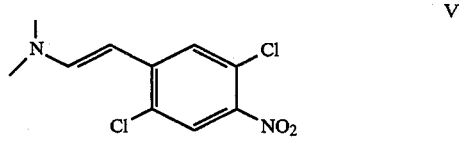

a. 1) with the compound of the formula

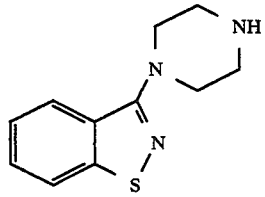

in the presence of a $(C_1-C_6)$ alkanoic acid to form the compound of the formula

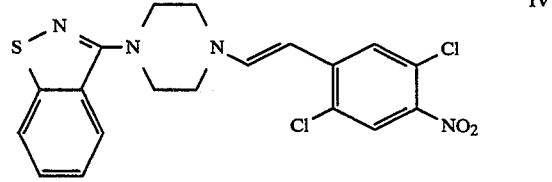

2) treating the compound of formula IV with a reducing agent to form the compound of the formula

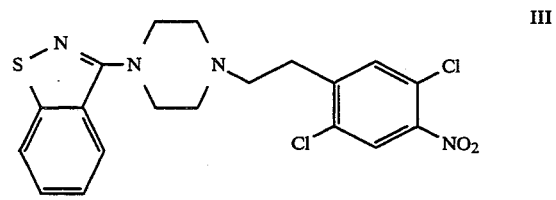

3) treating the compound of formula III with a compound of the formula $R^2$—$CH_2$—$CO_2R^1$ wherein $R^2$ is $CO_2R^1$ or CN and $R^1$ is $(C_1-C_6)$alkyl to form a compound of formula

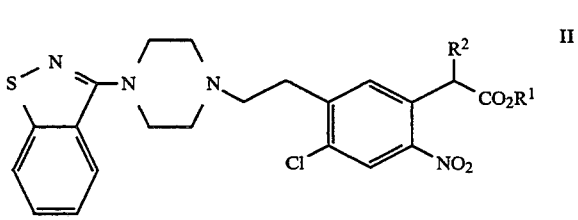

wherein $R^2$ is CN or $CO_2R^1$ and $R^1$ is $(C_1-C_6)$alkyl;

4) treating the product of step 3) with an acid at an elevated temperature to form a the compound of formula II wherein $R^2$ and $R^1$ are both hydrogen; and 5) treating the product of step 4 with a $(C_1-C_6)$alkanol in the presence of an acidic esterification catalyst to form the compound of formula II wherein $R^2$ is hydrogen and $R^1$ is $(C_1-C_6)$alkyl; or b) 1) treating the compound of formula V with a weak acid to form the compound of formula

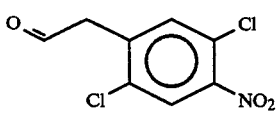

2) treating the compound of formula X with the compound of the formula

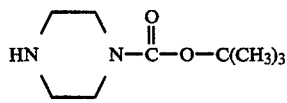

in the presence of $(CH_3CO_2)_3NaBH$ and acetic acid to form the compound of formula

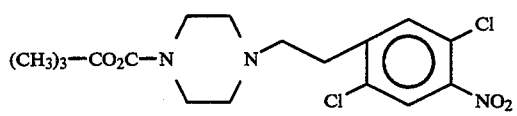

3) treating the compound of formula IX with a compound of the formula $R^2-CH_2-CO_2R^1$ wherein $R^2$ is $CO_2R^1$ or CN and $R^1$ is $(C_1-C_6)$alkyl to form a compound of formula

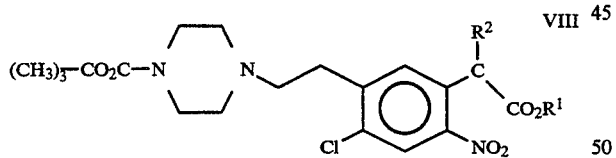

wherein $R^2$ is $CO_2R^1$ or CN and $R^1$ is $(C_1-C_6)$alkyl;

4) treating the compound of formula VIII with an acid at an elevated temperature to form the compound of formula

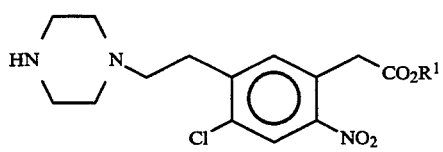

wherein $R_1$ is $(C_1-C_6)$alkyl; and 5) treating the compound of formula VII with the compound of formula

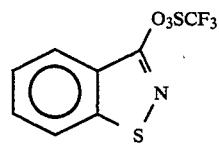

in the presence of a base to form the compound of formula II wherein $R^2$ is hydrogen and $R^1$ is $(C_1-C_6)$alkyl; and II. treating a compound of the formula

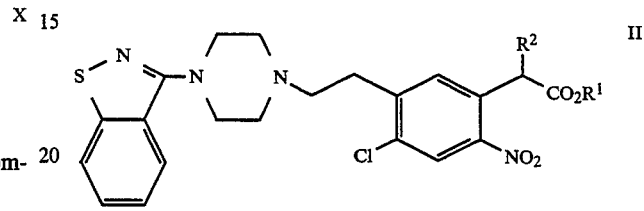

wherein $R^2$ is hydrogen, CN or $CO_2R^1$ and $R^1$ is hydrogen or $(C_1-C_6)$alkyl with a reducing agent with the proviso that when $R^2$ is CN or $CO_2R^1$ and $R^1$ is $(C_1-C_6)$alkyl the product of the reduction is heated with an acid.

Compounds of the formulae II and III wherein $R^1$ and $R^2$ are as defined above are novel and additional features of the invention.

DETAILED DESCRIPTION OF THE INVENTION

The processes of the instant invention are illustrated in schemes 1 and 2.

SCHEME 1

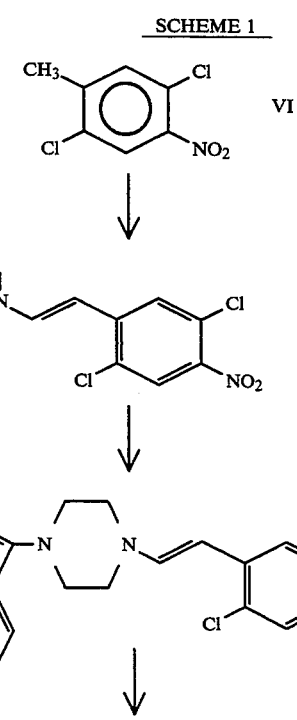

7
-continued
SCHEME 1

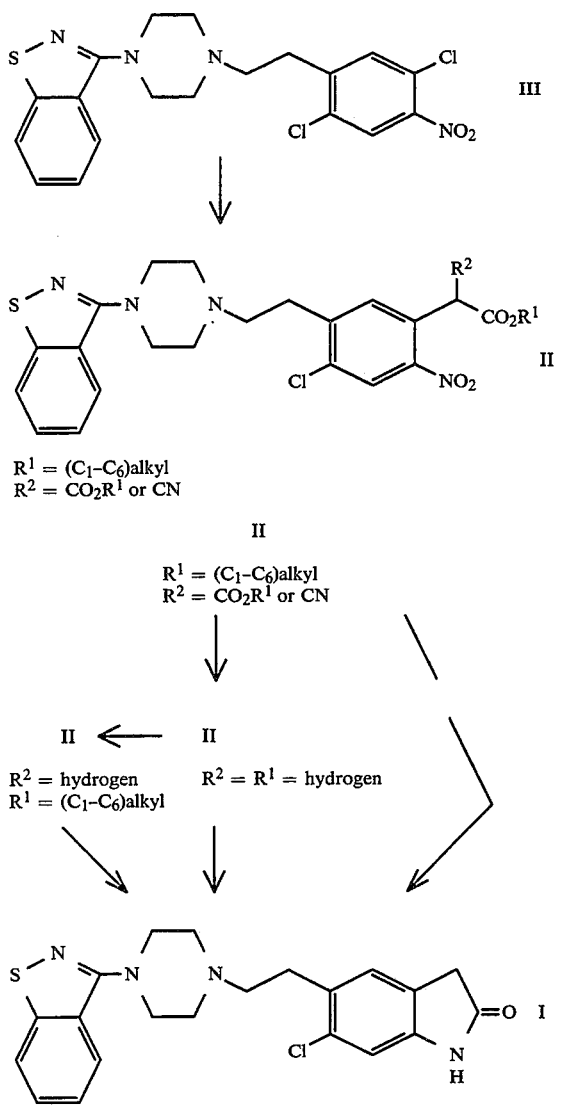

R$^1$ = (C$_1$-C$_6$)alkyl
R$^2$ = CO$_2$R$^1$ or CN

II

R$^1$ = (C$_1$-C$_6$)alkyl
R$^2$ = CO$_2$R$^1$ or CN

II ← II
R$^2$ = hydrogen    R$^2$ = R$^1$ = hydrogen
R$^1$ = (C$_1$-C$_6$)alkyl

SCHEME 2

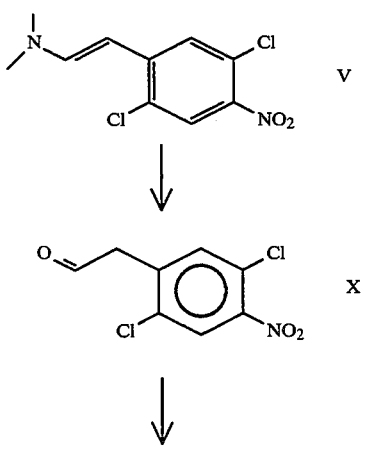

8
-continued
SCHEME 2

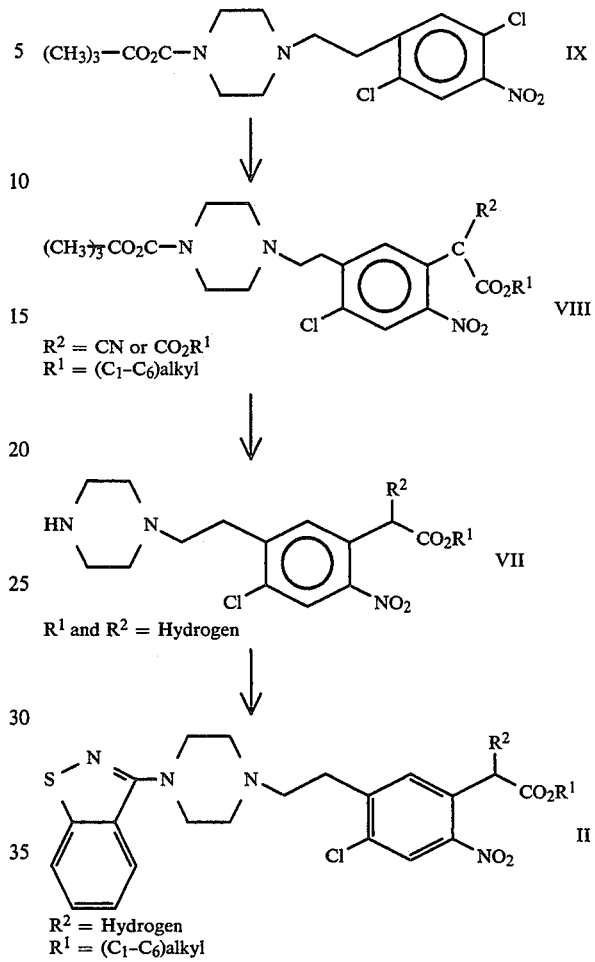

R$^2$ = CN or CO$_2$R$^1$
R$^1$ = (C$_1$-C$_6$)alkyl

R$^1$ and R$^2$ = Hydrogen

R$^2$ = Hydrogen
R$^1$ = (C$_1$-C$_6$)alkyl

As shown in Scheme 1 a compound of the formula II wherein R$^2$ is CN or CO$_2$R$^1$ and R$^1$ is (C$_1$-C$_6$)alkyl is treated with a reducing agent and the resulting product is heated with an acid to prepare compound of formula I. Generally the reaction is carried out in a reaction inert solvent. Suitable reducing agents are sodium hydrosulfite, hydrogen in the presence of a hydrogenation catalyst, iron in acetic acid, zinc and CaCl$_2$ in acetic acid and NaH$_2$PO$_2$ in the presence of Pd/C. A preferred reducing agent is sodium hydrosulfite. The temperature of the reduction stage is from about 10° to about 100° C. When sodium hydrosulfite is the reducing agent the reaction temperature is preferably from about 65° to about 80° C. The temperature at the acid treatment stage is from about 50° to about 110° C. Acids which are useful in this stage are strong mineral acids such as concentrated hydrochloric and 6N sulfuric acids. Suitable solvents are water and water miscible solvents such as (C$_1$-C$_6$)alkanols, tetrahydrofuran (THF) and dioxane and mixtures thereof.

Alternatively, a compound of formula II wherein R$^2$ is hydrogen and R$^1$ is hydrogen or (C$_1$-C$_6$)alkyl is converted to the compound of formula I by treatment with a reducing agent. Suitable conditions for the reduction are indicated above.

The compounds of formula II wherein R$^2$ is CN or CO$_2$R$^1$ and R$^1$ is (C$_1$-C$_6$)alkyl are prepared by reacting the compound of formula III with a compound of the formula $R^2$—$CH_2$—$CO_2R^1$, wherein $R^1$ is $(C_1-C_6)$alkyl and $R^2$ is CN or $CO_2R^1$, respectively, in the presence of a base. The reaction is, generally, effected in an aprotic polar solvent such as dimethylformamide (DMF), dimethylsulfoxide (DMSO) or N-methylpyrrolidone at a temperature from about 25° to about 100° C. Suitable bases include alkali metal hydroxides and hydrides and hindered $(C_1-C_6)$alkoxides such as KOH, NaOH, NaH and potassium-t-butoxide.

The compound of formula II wherein $R^2$ and $R^1$ are each hydrogen is prepared by heating a compound of formula II wherein $R^2$ is CN or $CO_2R^1$ and $R^1$ is $(C_1-C_6)$alkyl with an acid. The conditions and compositions for use in this process are as indicated above.

The compound of formula II wherein $R^2$ is hydrogen and $R^1$ is $(C_1-C_6)$alkyl is prepared by treating the compound of the formula II wherein $R^2$ and $R^1$ are each hydrogen with a $(C_1-C_6)$alkanol in the presence of an acidic esterification catalyst. Suitable esterification catalysts include sulfuric acid, p-toluenesulfonic acid, trifluoromethanesulfonic and thionyl chloride. The reaction is generally carried out at a temperature from about 25° to about 110° C. in a solvent such as a $(C_1-C_6)$alkanol neat or diluted with a halogenated hydrocarbon or an aromatic hydrocarbon such as $CH_2Cl_2$, $CHCl_2$, $CHCl_3$ and toluene.

The compound of formula III is prepared by reducing the compound of formula IV. Suitable reducing agents include sodium triacetoxyborohydride and sodium cyanoborohydride. The reaction is effected in the presence of a $(C_1-C_6)$alkanoic acid such as acetic acid. Suitable solvents for use in this process include halogenated hydrocarbons such as $CH_2Cl_2$ and 1,2-dichloroethane and aprotic polar solvents such as THF, DMF and DMSO. The reaction may be carried out at a temperature from about 0° to about 75° C.

The compound of formula IV is prepared by reacting the compound of the formula V with the compound of the formula

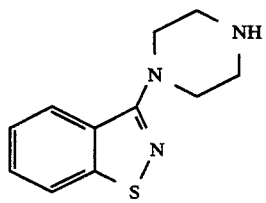

in the presence of a $(C_1-C_6)$alkanoic acid such as acetic acid. The reaction is usually carried out in solvents which include acetic acid, DMF, DMSO and THF at temperatures from about 20° to about 100° C.

The compound of formula V is prepared by treating the compound of the formula VI with an enamine forming compound either neat or in inert solvents such as aprotic polar solvents. Enamine forming compounds include t-butoxybis(dimethylamino)methane and dimethylformamide dialkylacetals. Preferred enamine compounds are t-butoxy-bis(dimethylamino)methane and dimethylformamide dimethylacetal. Solvents for use in this reaction include THF, DMF and the neat reagent. Preferred conditions are those wherein the enamine forming compounds are t-butoxy-bis(dimethylamino)methane and dimethylformamide dimethylacetal and the solvents are THF and DMF, respectively.

As shown in Scheme 2 the compound of formula II wherein $R^2$ is hydrogen and $R^1$ is $(C_1-C_6)$alkyl may, alternatively, be prepared by reacting a compound of the formula VII, wherein $R^1$ and $R^2$ are as defined above, with the compound of the formula

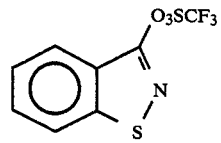

in the presence of a base. Suitable bases for use in this aspect of the invention include trialkylamines and cycloheteroarylamines such as triethylamine, pyridine and N-methylmorpholine. The reaction is usually carried out in inert solvents which include aprotic polar solvents such as THF, DMF and DMSO and halogenated hydrocarbons such as $CH_2Cl_2$ at temperatures from about 0° to about 50° C.

The compound of formula VII is prepared by reacting a compound of formula VIII wherein $R^2$ is CN or $CO_2R^1$ and $R^1$ is $(C_1-C_6)$alkyl with an acid at a temperature from about 50° to about 110° C. Suitable acids include concentrated hydrochloric acid and sulfuric acid. Solvents which may be used for this reaction include the acid reagent, e.g., the concentrated hydrochloric or sulfuric acid, which can be diluted with a $(C_1-C_4)$alkanoic acid.

The compound of formula VIII may be prepared by reacting the compound of formula IX with a compound of the formula $R^2$—$CH_2$—$CO_2R^1$, wherein $R^1$ is $(C_1-C_6)$alkyl and $R^2$ is CN or $CO_2R^1$, in the presence of a base. Suitable bases include alkali metal hydrides, hydroxides and hindered $(C_1-C_6)$alkoxides, such as KOH, NaH and potassium t-butoxide. The reaction is generally effected in a solvent such as DMF, DMSO or N-methylpyrrolidine at a temperature from about 25° to about 75° C.

The compound of formula IX is prepared by reacting the compound of the formula X with the compound of formula

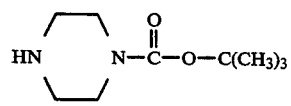

in the presence of $(CH_3CO_2)_3NaBH$ and acetic acid. Solvents useful in this aspect of the invention include halogenated hydrocarbons and such as methylene chloride and 1,2-dichloroethane and aprotic polar solvents such as THF, DMF and DMSO.

The compound of formula X is prepared by reacting the compound of formula V with a mild organic or mineral acid solution such as acetic or oxalic acid or dilute (0.5-1N) hydrochloric or sulfuric acid, in appropriate solvents such as water, halogenated hydrocarbons and hexanes, at a temperature from about 0° to about 50° C.

The neuroleptic activity of the compound of formula I may be demonstrated by methods based on standard procedures. In one method, adult male Sprague-Dawley rats are pretreated with appropriate doses of the test compound by subcutaneous injection. One half hour later, all rats are injected intraperitoneally with 1 mg/kg apomorphine hydrochloride dissolved in an 0.1% ascorbate solution and their behavior evaluated.

The neuroleptic activity of the compound of formula I makes it useful for treating psychotic disorders in human subjects. For example, the compound is useful for treating psychotic disorders of the schizophrenic types, and in particular the compound is useful for removing or ameliorating such symptoms as anxiety, agitation, excessive aggression, tension, and social or emotional withdrawal in psychotic patients.

The compound of formula I, or a pharmaceutically-acceptable salt thereof, can be administered to a human subject either alone or, preferably, in combination with pharmaceutically-acceptable carriers or diluents, in a pharmaceutical composition, according to standard pharmaceutical practice. The compound can be administered orally or parenterally. Parenteral administration includes, especially, intravenous and intramuscular administration. Additionally, in a pharmaceutical composition comprising the compound of formula I, or a pharmaceutically-acceptable salt thereof, the weight ratio of active ingredient to carrier will normally be in the range from 1:6 to 2:1, and preferably 1:4 to 1:1. However, in any given case, the ratio chosen will depend on such factors as the solubility of the active component, the dosage contemplated and the precise route of administration.

For oral use the compound of formula I can be administered, for example, in the form of tablets or capsules, or as an aqueous solution or suspension. For intramuscular and intravenous use, sterile solutions of the active ingredient can be prepared, and the pH of the solutions should be suitably adjusted and buffered. For intravenous use, the total concentration of solutes should be controlled to render the preparation isotonic.

When the neuroleptic agent of formula I is to be used in a human subject to treat a psychotic disorder, the daily dosage will normally be determined by the prescribing physician. Moreover, the dosage will vary according to the age, weight and response of the individual patient as well as the severity of the patient's symptoms. However, in most instances, an effective amount for treating a psychotic disorder will be a daily dosage in the range from 5 to 500 mg, and preferably 50 to 100 mg, in single or divided doses, orally or parenterally.

The following examples are provided solely for the purpose of further illustration.

EXAMPLE 1

2,5-Dichloro-4-methyl-nitrobenzene

Prepared by a modification of the method of H. D. Dakin and J. B. Cohen, *J. Chem. Soc.*, 79, 1130 (1901). 2,5-Dichlorotoluene (18.7 g, 0.116 mol) was added in one portion to a 10° C. mixture of concentrated sulfuric acid (24 ml) and glacial acetic acid (10 ml). This was stirred at about 10° C. while a cold mixture of 70% nitric acid (8.2 ml) and concentrated sulfuric acid (8.2 ml) was added dropwise over 10 min. The reaction mixture was warmed slowly to room temperature and stirred for 2 hours. The reaction mixture was then re-cooled to 10° C. with an ice bath and quenched with ice and methylene chloride. The layers were separated and the aqueous layer extracted with methylene chloride. The combined organic layers were washed two times with water, two times with saturated sodium bicarbonate solution and one time with brine. After drying over magnesium sulfate, the solvent was evaporated in vacuo and the crude product crystallized from isopropanol (30 ml). The yield of light yellow solid was 13.4 g, 56%; NMR (CDCl$_3$) δ 7.91 (s, 1), 7.42 (s, 1), 2.43 (s, 3).

EXAMPLE 2

2,5-Dichloro-4-(2-dimethylaminoethenyl)-nitrobenzene 2,5-Dichloro-4-methyl-nitrobenzene (50 g, 0.24 mol) was heated at reflux, in tetrahydrofuran (200 ml), with t-butoxy-bis(dimethylamino)methane (63.3 g, 0.364 mol) for 8 hours. The reaction mixture was cooled to room temperature and slowly poured into hexanes (3L) with stirring. The desired product was collected by filtration as a dark red solid, 36.9 g, 58% yield. mp 173°–5° C. NMR (CDCl$_3$) δ 8.01 (s, 1), 7.32 (s, 1), 7.08 (d, 1), 5.27 (d, 1), 3.00 (s, 6). Analysis Calculated for C$_{10}$H$_{10}$N$_2$O$_2$Cl$_2$: C, 45.99; H, 3.86; N, 10.73, Found: C, 45.91; H, 3.72; N, 10.61.

EXAMPLE 3

2,5-Dichloro-4-(2-[4-(1,2-benzisothiazol-3-yl)-1-piperazinyl]ethenyl)-nitrobenzene 2,5-Dichloro-4-(2-dimethylaminoethenyl)-nitrobenzene (15 g, 0.057 mol) and 4-(1,2-benzisothiazol-3-yl)-piperazine (18.9 g, 0.086 mol) were combined in acetic acid (150 ml) and stirred overnight at room temperature under a nitrogen atmosphere. The slurry was poured slowly into a mixture of hexanes (300 ml) and isopropanol (300 ml) with stirring. The product was isolated by filtration as a brick red solid and washed with hexanes. The yield was 23.4 g, 93%; mp 194°–5° C. NMR (CDCl$_3$) δ 8.05 (s, 1), 7.95–7.80 (m, 2), 7.56–7.35 (m, 3), 7.01 (d, 1), 5.60 (d, 1), 3.95–3.46 (m, 8). Analysis Calculated for C$_{19}$H$_{16}$N$_4$O$_2$Cl$_2$S: C, 52.41; H, 3.70; N, 12.87. Found: C, 52.05; H, 3.36; N, 12.58.

EXAMPLE 4

2,5-Dichloro-4-(2-[4-(1,2-benzisothiazol-3-yl)-1-piperazinyl]ethyl)-nitrobenzene The enamine from the preceding example (22.5 g, 0.052 mol) was suspended in 1,2-dichloroethane (340 ml) with acetic acid (17.8 ml) and stirred under a nitrogen atmosphere while sodium triacetoxyborohydride (21.9 g, 0.1 mol) was added in portions as a solid. The reaction was stirred overnight. Aqueous sodium carbonate solution was then added to the reaction mixture and then ethyl acetate (300 ml). The layers were separated and the aqueous layer extracted a second time with ethyl acetate. The combined organic layers were washed with water and brine and dried over magnesium sulfate. The crude product was isolated from the organic solution and purified by recrystallization from acetonitrile; 16.14 g, 71% yield. mp 153°–7° C. NMR (CDCl$_3$) δ 7.97 (s, 1), 7.91 (d, 1), 7.82 (d, 1), 7.50 (s, 1), 7.48 (dd,1), 7.37 (dd, 1), 3.58 (m, 4), 3.00 (t, 2), 2.78 (m, 4), 2.72 (t, 2). Analysis Calculated for C$_{19}$H$_{18}$N$_4$O$_2$Cl$_2$S: C, 52.18; H, 4.15; N, 12.81. Found: C, 51.97; H, 3.98; N, 12.65. The structure was confirmed by single crystal x-ray analysis.

EXAMPLE 5

5-Chloro-4-(2-[4-(1,2-benzisothiazol-3-yl)-1-piperazinyl]ethyl)-2-(bis-(methoxycarbonyl)methyl)-nitrobenzene 2,5-Dichloro-4-(2-[4-(1,2-benzisothiazol-3-yl)-1-piperazinyl]ethyl)-nitrobenzene (2.4 g, 55 mmol) and dimethylmalonate (1.81 g, 137 mmol) were dissolved in N-methyl-pyrrolidine (24 ml) and a stream of nitrogen was bubbled through the solution for 15 minutes to remove any oxygen. Powdered potassium hydroxide (0.77 g, 137 mmol) was added in one portion and the mixture heated at 40°–5° C. for 5 hours. The reaction mixture was cooled and diluted with ethyl acetate and washed with saturated ammonium chloride solution, water, and brine. The organic layer was dried over magnesium sulfate, filtered and evaporated to afford the crude product. The pure product was isolated by flash chromatography over silica gel with ethyl acetate/hexanes (4:6) as a light yellow solid, 1.32 g, 45% yield. mp 128°–31° C. NMR (CDCl$_3$) δ 8.10 (s, 1), 7.90 (d, 1), 7.81 (d, 1), 7.48 (t and s, 2), 7.37 (t, 1), 5.33 (s, 1), 3.82 (s, 6), 3.58 (m, 4), 3.06 (t, 2), 2.80–2.70 (m, 6). The structure was confirmed by single crystal x-ray analysis.

EXAMPLE 6

5-(2-[4-(1,2-Benzisothiazol-3-yl)-1-piperazinyl]ethyl)-4-chloro-2-nitrophenyl acetic acid The 2-nitrophenyl-malonate (4.4 g, 83 mmol) from the previous example was refluxed in 3N hydrochloric acid (90 ml) for 20 hours. The reaction mixture was cooled and the precipitated product isolated by filtration and dried in vacuo; 4 g, 95%.mp 209°–212° C. (dec). NMR (DMSO-d$_6$) δ 8.21 (s, 1), 8.15 (d, 1), 8.0 (d,1), 7.67 (s, 1), 7.59 (t, 1), 7.48 (t, 1), 4.10 (br d, 2), 4.00 (s, 2), 3.79–3.23 (m, 8).

EXAMPLE 7

Methyl 5-(2-[4-(1,2-benzisothiazol-3-yl)-1-piperazinyl]ethyl)-4-chloro-2-nitrophenyl acetate Methanol (62 ml) was stirred at −10° C. under a nitrogen atmosphere. Thionyl chloride (1 ml, 135 mmol) was added slowly, dropwise, to the methanol and then the product from the previous reaction was added in one portion as a solid. The cooling was removed and the reaction heated to reflux for 3 hours. The reaction mixture was evaporated in vacuo to remove the methanol and then partitioned between ethyl acetate and aqueous sodium carbonate. The aqueous layer was extracted a second time with ethyl acetate. The combined organic layers were washed with brine, dried over magnesium sulfate and evaporated to give the desired amino acid ester as an oil; 3 g, 94% yield. NMR (CDCl$_3$) δ 8.18 (s, 1), 7.90 (d, 1), 7.81 (d, 1), 7.48 (t, 1), 7.36 (t, 1), 7.31 (s, 1), 4.00 (s, 2), 3.72 (s, 3), 3.63 (m, 4), 3.09 (m, 2), 2.89–2.72 (m, 6).

EXAMPLE 8

6-Chloro-5-(2-[4-(1,2-benzisothiazol-3-yl)-1-piperazinyl]ethyl)-oxindole

The title compound (2.4 g, 50 mmol) from the previous example was dissolved in a mixture of tetrahydrofuran (24 ml) and ethanol (24 ml). Water (16 ml) was added to the stirred solution followed by sodium hydrosulfite (2.03 g, 116 mmol) and the mixture was heated to reflux. After 10 minutes, the solids had dissolved and a second portion of sodium hydrosulfite (1.3 g, 76 mmol) and water were added. The reaction mixture was heated on a steam bath for 4 hours. The reaction mixture was cooled, 6N hydrochloric acid (8.4 ml) was added and the reaction mixture was again heated for 15 minutes on the steam bath. The reaction mixture was made basic with sodium carbonate and the crude product collected by filtration and recrystallized from tetrahydrofuran, 0.8 g, 40% yield. NMR (DMSO-d$_6$) δ 8.05 (d, 2), 7.55 (t, 1), 7.42 (t, 1), 7.21 (s, 1), 6.80 (s, 1), 3.45 (s, 2), 2.83 (m, 2), 2.70 (m, 4), 2.54 (m, 6). This was identical with product prepared previously.

EXAMPLE 9

Methyl [5-(2-[4-(1,2-benzisothiazol-3-yl)-1-piperazinyl]ethyl)-4-chloro-2-nitrophenyl]-cyanoacetate 2,5-Dichloro-4-(2-[4-(1,2-benzisothiazol-3-yl)-1-piperazinyl]ethyl)-nitrobenzene (1 g, 2.3 mmol) and methyl cyanoacetate (0.44 ml, 5 mmol) were dissolved in N-methylpyrrolidine (25 ml) under nitrogen. Powdered potassium hydroxide (0.28 g, 5 mmol) was added and the mixture was heated to 57° C. for 4 hours at which time tlc showed that the starting material had reacted. The cooled reaction mixture was poured into a stirred mixture of saturated aqueous ammonium chloride and ethyl acetate. The aqueous layer was adjusted to pH 6 with 2N hydrochloric acid and the layers were separated. The aqueous layer was extracted with ethyl acetate. The combined organic layers were washed with water and brine, dried and filtered. The ethyl acetate solution was concentrated to 20 ml and p-toluenesulfonic acid (0.44 g, 2.3 mmol) was added with stirring. The tosylate salt of the desired product was collected and dried in vacuo. The yield was 1.27 g, 82.5%. mp 204°–7° C. Analysis calculated for C$_{30}$H$_{30}$N$_5$O$_7$Cl$_2$S: C, 53.61; H, 4.50; N, 10.42. Found: C, 53.52; H, 4.15; N, 10.70.

The tosylate salt was dissolved in water and adjusted to a pH of 12 with 1N sodium hydroxide. The basic solution was extracted with ethyl acetate. The ethyl acetate was evaporated to yield the free base as a purple solid, mp 91°–100° C. NMR (CDCl$_3$) δ 8.27 (s, 1), 7.91 (d, 1), 7.82 (d, 1), 7.78 (s, 1), 7.49 (t, 1), 7.38 (t, 1), 5.68 (s, 1), 3.88 (m, 4), 3.1 (m, 2,), 2.8, (m, 6).

Hydrolysis of the tosylate salt or free base in concentrated hydrochloric acid at 100° C. provided a product identical with that from Example 6.

EXAMPLE 10

2,5-Dichloro-4-nitrophenylacetaldehyde 2,5-Dichloro-4-(2-dimethylaminoethenyl)-nitrobenzene (10 g, 38.3 mmol) was dissolved in methylene chloride (200 ml) and stirred with a solution of oxalic acid (14.5 g, 115 mmol) in water (80 ml) at room temperature for 18 hours. The layers were separated and the aqueous layer extracted with methylene chloride (50 ml). The combined organic layers were washed with water and brine, dried over magnesium sulfate and filtered. The solution was evaporated to yield the title compound. NMR (CDCl$_3$) δ 9.70 (s, 1), 8.01 (s, 1), 7.49 (s, 1), 3.98 (s, 2).

EXAMPLE 11

2,5-Dichloro-4-(2-[4-(t-butoxycarbonyl)-1-piperazinyl]ethyl)-nitrobenzene

A methylene chloride solution of the title compound of Example 10 was stirred at room temperature under nitrogen. Acetic acid (8.8 ml, 153 mmol) was added in one portion followed by t-butylpiperazinecarboxylate (8.4 g, 50 mmol). Sodium triacetoxy-borohydride (16.2 g, 77 mmol) was added in portions as a solid and the reaction mixture stirred at room temperature for three hours. The reaction mixture was washed two times with excess saturated sodium carbonate solution and one time each with water and brine. The organic layer was dried over magnesium sulfate, filtered and evaporated to afford the title product as an oil 15.6 g, (98% crude yield). This was suitable for use in the next reaction without further purification. NMR (CDCl3) δ 7.92 (s, 1), 7.48 (s, 1), 3.43 (m, 4), 2.97 (t, 2), 2.62 (t, 2), 2.49 (m, 4), 1.43 (s, 9).

EXAMPLE 12

5-Chloro-4-(2-[4-(t-butoxycarbonyl)-1-piperazinyl]ethyl)-2-(bis-(methoxycarbonyl)methyl)-nitrobenzene 2,5-Dichloro-4-(2-[4-(t-butoxycarbonyl)-1-piperazinyl]ethyl)-nitrobenzene (5 g, 13 mmol) and dimethyl malonate (3.8 ml, 33 mmol) were stirred in N-methyl pyrrolidone (75 ml), at room temperature under nitrogen, while sodium hydride (1.33 g, 33 mmol, 60% in oil) was added. The reaction mixture was heated to 57° C. for 7 hours. The reaction mixture was cooled and poured into saturated aqueous ammonium chloride solution and extracted twice with ethyl acetate. The combined organic layers were washed with water three times, one time with brine and dried over magnesium sulfate. Evaporation of the solvent in vacuo gave an oil which was chromatographed over flash silica gel with ethyl acetate/hexanes followed by ethyl acetate. The fractions containing the desired product were combined and evaporated to give an oil, 2.5 g, 48% yield. NMR (CDCl3) δ 8.09 (s, 1), 7.45 (s, 1), 5.31 (s, 1), 3.79 (s, 6), 3.43 (m, 4), 2.98 (t, 2), 2.61 (t, 2), 2.47 (m, 4), 1.43 (s, 9).

EXAMPLE 13

Methyl 5-(2-(1-piperazinyl)ethyl)-4-chloro-2-nitrophenyl acetate

5-Chloro-4-(2-[4-(t-butoxycarbonyl)-1-piperazinyl]ethyl)-2-(bis-(methoxycarbonyl)methyl)-nitrobenzene (2.5 g, 6.3 mmol) was refluxed for 5 hours in 6N hydrochloric acid. The reaction mixture was then stirred at room temperature overnight and evaporated in vacuo to a solid which was slurried in isopropanol and collected; NMR (D2O) δ 8.25 (s, 1), 7.40 (s, 1), 4.03 (s, 2), 3.8–3.25 (4 multiplets for piperazine and ethyl groups). The amino acid hydrochloride was dissolved in methanol (20 ml) and cooled in an ice bath while thionyl chloride (1 ml, 14 mmol) was added dropwise. The solution was heated at reflux for 2 hours then cooled and evaporated in vacuo to a foam. The crude product was partioned between ethyl acetate and water at pH 12. The organic layer was dried over sodium sulfate, filtered and evaporated to afford the desired ester as a dark oil, 1.34 g, 67% yield. NMR (CDCl3) δ 8.12 (s, 1), 7.22 (s, 1), 3.94 (s, 2), 3.71 (s, 3), 2.96 and 2.89 (m, 6), 2.58 and 2.49 (m, 6).

EXAMPLE 14

Methyl 5-(2-[4-(1,2-benzisothiazol-3-yl)-1-piperazinyl]ethyl)-4-chloro-2-nitrophenyl acetate Methyl 5-(2-(1-piperazinyl)ethyl)-4-chloro-2-nitrophenyl acetate (175 mg, 0.5 mmol) and 3-(trifluoromethylsulfonyloxy)-1,2-benzisothiazole (163 mg, 0.58 mmol) [prepared from 2,1-benzisothiazol-3(1H)-one with trifluoro-methanesulfonyl anhydride and pyridine in methylene chloride] were stirred in dry tetrahydrofuran (2.5 ml) with triethylamine (0.11 ml, 0.8 mmol) for 20 hours at room temperature. The reaction mixture was diluted with ethyl acetate and washed with aqueous sodium carbonate, water and brine. The organic layer was dried over magnesium sulfate, filtered, and evaporated in vacuo. The crude residue was chromatographed over flash silica gel with 10% ethyl acetate in chloroform to afford the desired product; 60 mg, 25% yield. This material was identical with that of Example 7.

What is claimed is:

1. A process for preparing a compound of the formula

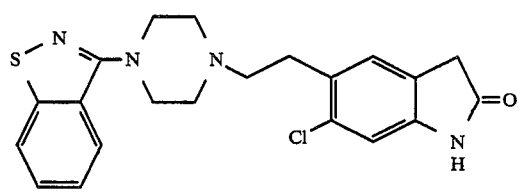

which comprises treating a compound of the formula

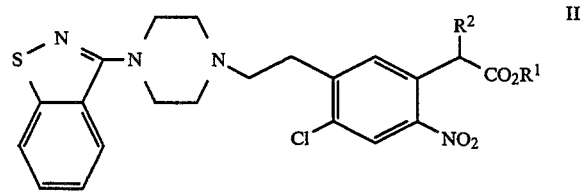

wherein $R^2$ is hydrogen, CN or $CO_2R^1$ and $R^1$ is hydrogen or ($C_1$–$C_6$)alkyl with a reducing agent selected from the group consisting of sodium hydrosulfite, hydrogen in the presence of a hydrogenation catalyst, iron in acetic acid, zinc and $CaCl_2$ in acetic acid and $NaH_2PO_2$ in the presence of Pd/C with the proviso that when $R^2$ is CN or $CO_2R^1$ and $R^1$ is ($C_1$–$C_6$) alkyl the product of the reduction is heated with an acid.

2. The process of claim 1 wherein said acid is selected from the group consisting of concentrated hydrochloric acid or concentrated hydrochloric acid diluted to 6N or 3N with water or acetic acid.

3. The process of claim 1 wherein said reduction is effect in an inert solvent selected from the group consisting of water, water miscible solvents and mixtures thereof.

4. The process of claim 1 wherein said reducing agent is sodium hydrosulfite and said solvent is THF.

5. The process of claim 1 wherein the compound of the formula II is prepared
   a) when $R^2$ and $R^1$ are both hydrogen by heating the compound of the formula II wherein $R^1$ is ($C_1$–$C_6$)alkyl and $R^2$ is CN or $CO_2R^1$ in the presence of an aqueous acid:
   b) when $R^2$ is hydrogen and $R^1$ is ($C_1$–$C_6$)alkyl by
      i) treating a compound of the formula

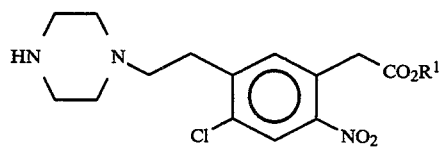

wherein $R^1$ is ($C_1$–$C_6$)alkyl with the compound of the formula

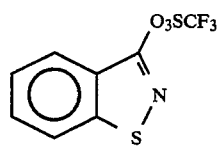

in the presence of a base; or ii) treating a compound of the formula II wherein $R^1$ and $R^2$ are both hydrogen with a $(C_1-C_6)$alkanol in the presence of an acidic esterification catalyst; or c) wherein $R^1$ is $(C_1-C_6)$alkyl and $R^2$ is CN or $CO_2R^1$ by treating the compound of the formula

III

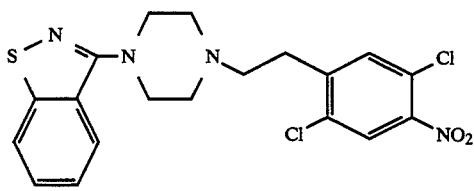

with a compound of the formula $R^2$—$CH_2$—$CO_2R^1$, wherein $R^2$ is CN or $CO_2R^1$, respectively, and $R^1$ is $(C_1-C_6)$alkyl in the presence of a base.

6. The process of claim 5 wherein the compound of formula III is prepared by treating the compound of the formula

IV

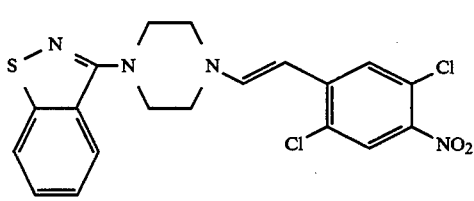

with a reducing agent.

7. The process of claim 5 wherein the compound of formula VII is prepared by treating a compound of the formula

VIII

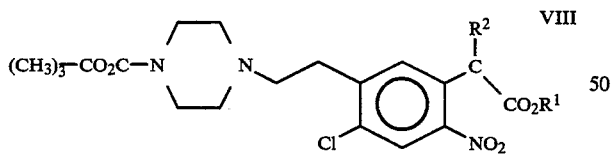

wherein $R^2$ is $CO_2R^1$ or CN and $R^1$ is $(C_1-C_6)$alkyl with an acid at an elevated temperature.

8. A process for preparing a compound of the formula

I

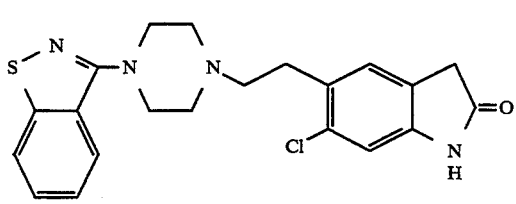

which comprises the steps of

I. treating a compound of the formula

V

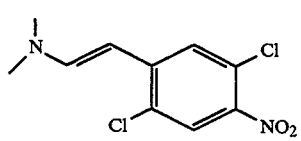

a) 1) with the compound of the formula

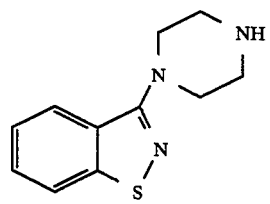

in the presence of a $(C_1-C_6)$ alkanoic acid to form the compound of the formula

IV

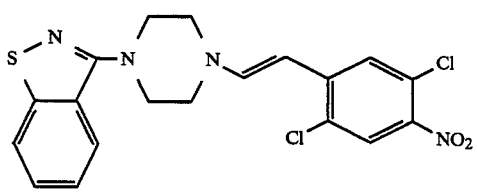

2) treating the compound of formula IV with a reducing agent to form the compound of the formula

III

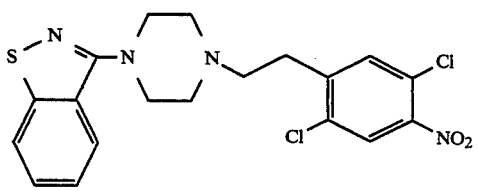

3) treating the compound of formula III with a compound of the formula $R^2$—$CH_2$—$CO_2R^1$ wherein $R^2$ is $CO_2R^1$ or CN and $R^1$ is $(C_1-C_6)$alkyl in the presence of a base to form a compound of formula

II

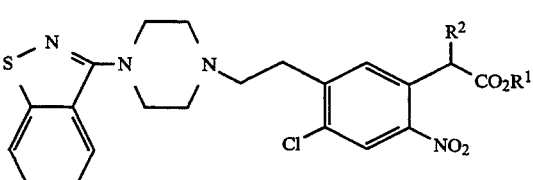

wherein $R^2$ is CN or $CO_2R^1$ and $R^1$ is $(C_1-C_6)$alkyl;

4) treating the product of step 3) with an acid at an elevated temperature to form the compound of formula II wherein $R^2$ and $R^1$ are both hydrogen; and 5) treating the product of step 4 with a $(C_1-C_6)$alkanol in the presence of an acidic esterification catalyst to form the compound of formula II wherein R² is hydrogen and R¹ is (C₁-C₆)alkyl; or b) 1) treating the compound of formula V with a weak acid to form the compound of formula

X 2) treating the compound of formula X with the compound of formula in the presence of (CH₃CO₂)₃NaBH and acetic acid to form the compound of formula

IX 3) treating the compound of formula IX with a compound of the formula R²—CH₂—CO₂R¹ wherein R² is CO₂R¹ or CN and R¹ is (C₁-C₆)alkyl in the presence of a base to form a compound of formula

VIII wherein R² is CO₂R¹ or CN and R¹ is (C₁-C₆)alkyl;

4) treating the compound of formula VIII with an acid at an elevated temperature to form the compound of formula

VII wherein R₁ is (C₁-C₆)alkyl; and 5) treating the compound of formula VII with the compound of formula in the presence of a base to form the compound of formula II wherein R² is hydrogen and R¹ is (C₁-C₆)alkyl; or II. treating a compound of the formula

II wherein R² is hydrogen, CN or CO₂R¹ and R¹ is hydrogen or (C₁-C₆)alkyl with a reducing agent with the proviso that when R² is CN or CO₂R¹ and R¹ is (C₁-C₆)alkyl the product of the reduction is heated with an acid.

9. A compound of the formula

II wherein R¹ is hydrogen or (C₁-C₆)alkyl and R² is hydrogen, CN or CO₂R¹.

10. The compound of claim 9 wherein R¹ is (C₁-C₆)alkyl and R² is CN or CO₂R¹.

11. The compound of claim 10 wherein R¹ is methyl.

12. The compound of claim 9 wherein R² is hydrogen.

13. The compound of claim 12 wherein R¹ is hydrogen.

14. The compound of claim 12 wherein R¹ is CH₃.

15. The compound of the formula

III

16. The compound of the formula

VII wherein R¹ is (C₁-C₆)alkyl.

17. The compound of claim 16 wherein R¹ is methyl.

* * * * *